United States Patent
Sigmon, Jr.

(10) Patent No.: US 8,758,264 B2
(45) Date of Patent: Jun. 24, 2014

(54) EXPANDABLE DEVICE FOR FULL THICKNESS BIOPSY

(75) Inventor: John C. Sigmon, Jr., Winston-Salem, NC (US)

(73) Assignee: Cook Medical Technologies LLC, Bloomington, IN (US)

(*) Notice: Subject to any disclaimer, the term of this patent is extended or adjusted under 35 U.S.C. 154(b) by 178 days.

(21) Appl. No.: 13/534,209

(22) Filed: Jun. 27, 2012

(65) Prior Publication Data

US 2013/0006141 A1 Jan. 3, 2013

Related U.S. Application Data

(60) Provisional application No. 61/502,581, filed on Jun. 29, 2011.

(51) Int. Cl.
*A61B 10/00* (2006.01)

(52) U.S. Cl.
USPC ........... 600/562; 600/564; 600/566; 600/567; 600/568

(58) Field of Classification Search
USPC .......................... 600/562, 564, 566, 567, 568
See application file for complete search history.

(56) References Cited

U.S. PATENT DOCUMENTS

| | | | | | |
|---|---|---|---|---|---|
| 3,732,858 | A * | 5/1973 | Banko | ............ | 600/566 |
| 4,706,671 | A * | 11/1987 | Weinrib | ............ | 606/159 |
| 4,785,826 | A * | 11/1988 | Ward | ............ | 600/567 |
| 4,935,025 | A * | 6/1990 | Bundy et al. | ............ | 606/180 |
| 5,074,311 | A * | 12/1991 | Hasson | ............ | 600/567 |
| 5,573,008 | A * | 11/1996 | Robinson et al. | ............ | 600/567 |
| 5,630,805 | A * | 5/1997 | Ternamian | ............ | 604/274 |
| 5,660,186 | A * | 8/1997 | Bachir | ............ | 600/562 |
| 6,162,203 | A * | 12/2000 | Haaga | ............ | 604/272 |
| 6,544,195 | B2 * | 4/2003 | Wilson et al. | ............ | 600/564 |
| 6,626,903 | B2 * | 9/2003 | McGuckin et al. | ............ | 606/45 |
| 6,716,179 | B2 * | 4/2004 | Burbank et al. | ............ | 600/564 |
| 6,827,692 | B2 * | 12/2004 | Castellacci | ............ | 600/567 |
| 6,971,988 | B2 * | 12/2005 | Orban, III | ............ | 600/104 |
| 7,063,671 | B2 * | 6/2006 | Couvillon, Jr. | ............ | 600/562 |
| 8,157,812 | B2 * | 4/2012 | Barr | ............ | 606/116 |
| 8,529,563 | B2 * | 9/2013 | Long et al. | ............ | 606/41 |
| 8,574,220 | B2 * | 11/2013 | Frassica et al. | ............ | 604/528 |
| 2002/0115943 | A1 * | 8/2002 | Burbank et al. | ............ | 600/562 |
| 2005/0010275 | A1 * | 1/2005 | Sahatjian et al. | ............ | 623/1.11 |
| 2005/0143674 | A1 * | 6/2005 | Burbank et al. | ............ | 600/564 |
| 2005/0209530 | A1 * | 9/2005 | Pflueger | ............ | 600/567 |
| 2005/0245842 | A1 * | 11/2005 | Burbank et al. | ............ | 600/564 |
| 2006/0030847 | A1 * | 2/2006 | McGuckin et al. | ............ | 606/47 |
| 2006/0235333 | A1 * | 10/2006 | Couvillon | ............ | 600/562 |
| 2008/0125798 | A1 * | 5/2008 | Osborne et al. | ............ | 606/159 |
| 2008/0234602 | A1 * | 9/2008 | Oostman et al. | ............ | 600/564 |
| 2008/0294181 | A1 * | 11/2008 | Wensel et al. | ............ | 606/159 |
| 2009/0054805 | A1 * | 2/2009 | Boyle, Jr. | ............ | 600/564 |
| 2009/0124927 | A1 * | 5/2009 | Chin et al. | ............ | 600/562 |
| 2009/0131815 | A1 * | 5/2009 | Zimmer et al. | ............ | 600/562 |
| 2010/0152609 | A1 * | 6/2010 | Zwolinski et al. | ............ | 600/566 |

* cited by examiner

*Primary Examiner* — Rene Towa
*Assistant Examiner* — May Abouelela
(74) *Attorney, Agent, or Firm* — Brinks Gilson & Lione

(57) ABSTRACT

An expandable biopsy device and a method of obtaining a biopsy sample are provided. The expandable biopsy device includes an expandable portion including an expandable plate member and a cable operably connected to the expandable plate member. The expandable plate member has a substantially flattened configuration and an expanded configuration where the expanded configuration is longitudinally elongated relative to the flattened configuration. The flattened configuration has a first diameter. The expandable biopsy device also includes a cutting portion including a blade and a housing. The blade is positionable at least partially within the housing and the blade has a second diameter. The housing includes an opening and a cavity formed within housing. The second diameter of the blade is greater than the first diameter of the expandable plate member in the substantially flattened configuration.

19 Claims, 9 Drawing Sheets

EXPANDABLE DEVICE FOR FULL THICKNESS BIOPSY

RELATED APPLICATIONS

This application claims the benefit of U.S. Provisional Application No. 61/502,581, filed Jun. 29, 2011, which is incorporated by reference herein in its entirety.

BACKGROUND

Full thickness gastric wall biopsies that include the entire muscularis propria would be helpful to evaluate a number of diseases including motility abnormalities and cancer. Current mucosal-based biopsies are insufficient as they do not allow evaluation of the deep muscle layers or neural tissue including ganglia present in the deep layers. At present, most full thickness biopsies require invasive surgical procedures to access the gastric wall and other deep tissue areas.

What is needed in the art is a full thickness biopsy device that is less surgically invasive. What is needed in the art is a minimally invasive device that can obtain a full thickness biopsy device using an endoscopic procedure.

BRIEF SUMMARY

Accordingly, it is an object of the present invention to provide a device and a method having features that resolve or improve on the above-described drawbacks.

In one aspect, an expandable biopsy device is provided. The expandable biopsy device includes an expandable portion including an expandable plate member and a cable operably connected to the expandable plate member. The expandable plate member has a substantially flattened configuration and an expanded configuration where the expanded configuration is longitudinally elongated relative to the flattened configuration. The flattened configuration has a first diameter. The expandable biopsy device also includes a cutting portion including a blade and a housing. The blade is positionable at least partially within the housing and the blade has a second diameter. The housing includes an opening and a cavity formed within housing. The second diameter of the blade is greater than the first diameter of the expandable plate member in the substantially flattened configuration.

In another aspect, a method of obtaining a biopsy sample is provided. The method includes positioning an expandable portion of a biopsy device at a tissue site. The expandable portion includes an expandable plate member and a cable operably connected to the expandable plate member where the expandable plate member has a substantially flattened configuration and an expanded configuration. The method further includes inserting the expandable plate member into the tissue site in the expanded configuration and proximally pulling on the cable and positioning the expandable plate member in the flattened configuration at the tissue site. The method also includes advancing a cutting portion of the biopsy device toward the tissue site over the cable, advancing a blade of the cutting portion to the tissue site and cutting the tissue sample while holding the expandable plate member against the tissue sample in the flattened configuration.

DETAILED DESCRIPTION

Figure 1:
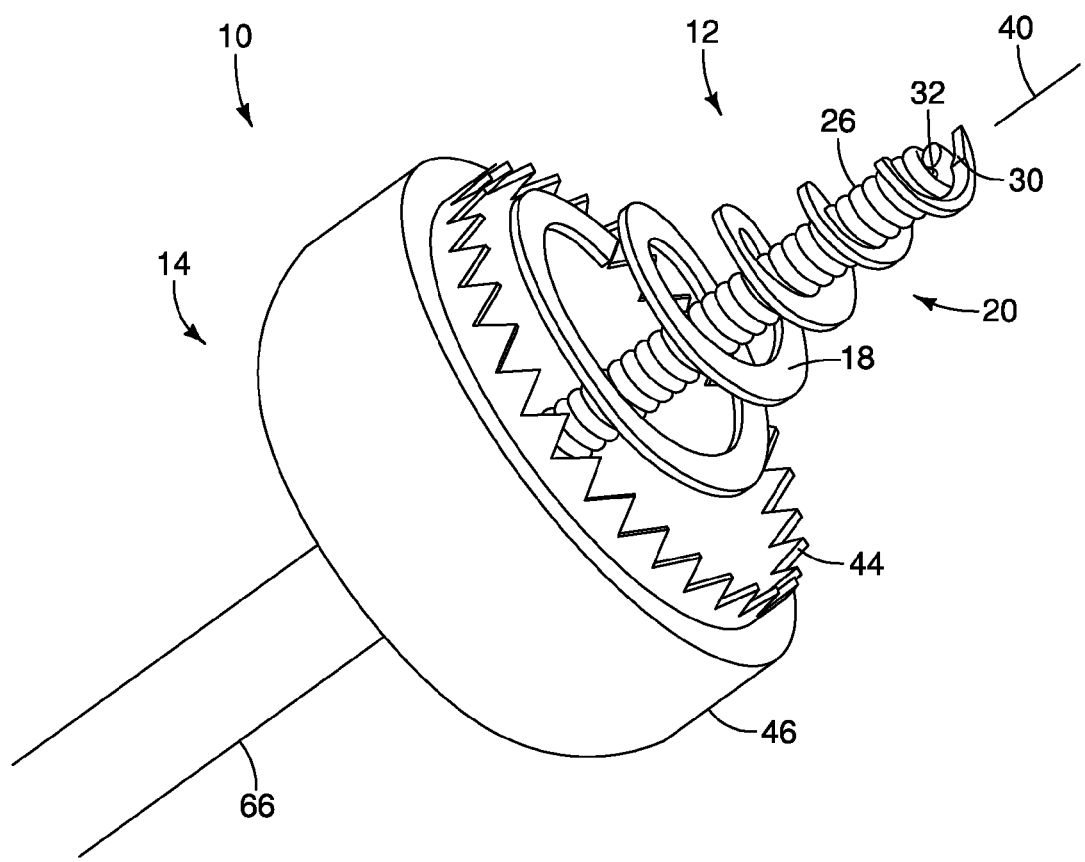
FIG. 1 is a perspective view of an expandable biopsy device in accordance with an embodiment of the present invention.

The invention is described with reference to the drawings in which like elements are referred to by like numerals. The relationship and functioning of the various elements of this invention are better understood by the following detailed description. However, the embodiments of this invention are not limited to the embodiments illustrated in the drawings. It should be understood that the drawings are not to scale, and in certain instances details have been omitted which are not necessary for an understanding of the present invention, such as conventional fabrication and assembly.

As used in the specification, the terms proximal and distal should be understood as being in the terms of a physician delivering the expandable biopsy device to a patient. Hence the term "distal" means the portion of the expandable biopsy device that is farthest from the physician and the term "proximal" means the portion of the expandable biopsy device that is nearest to the physician.

Figure 2:
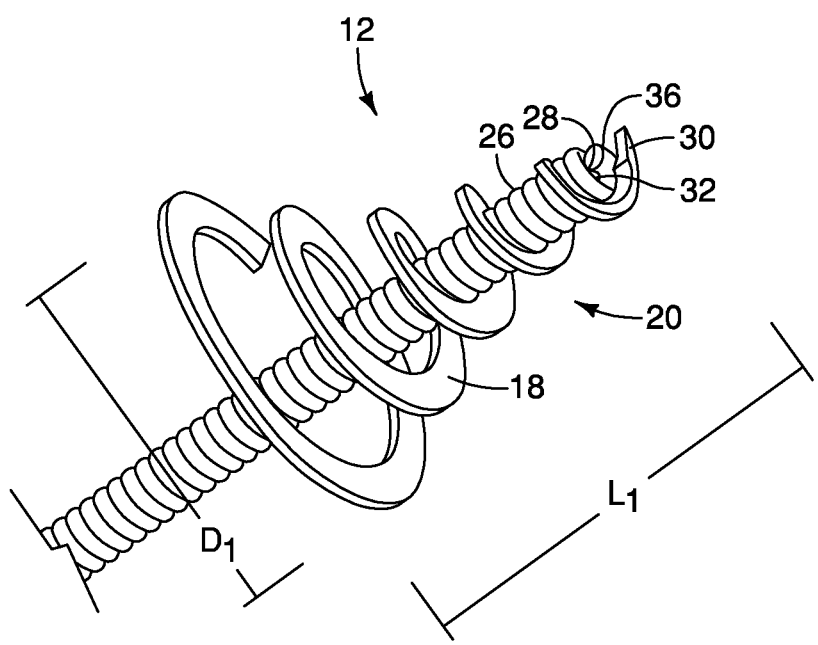
FIG. 2 is a partial perspective view of an expandable portion of the expandable biopsy device shown in FIG. 1 in an expanded configuration.
Figure 3:
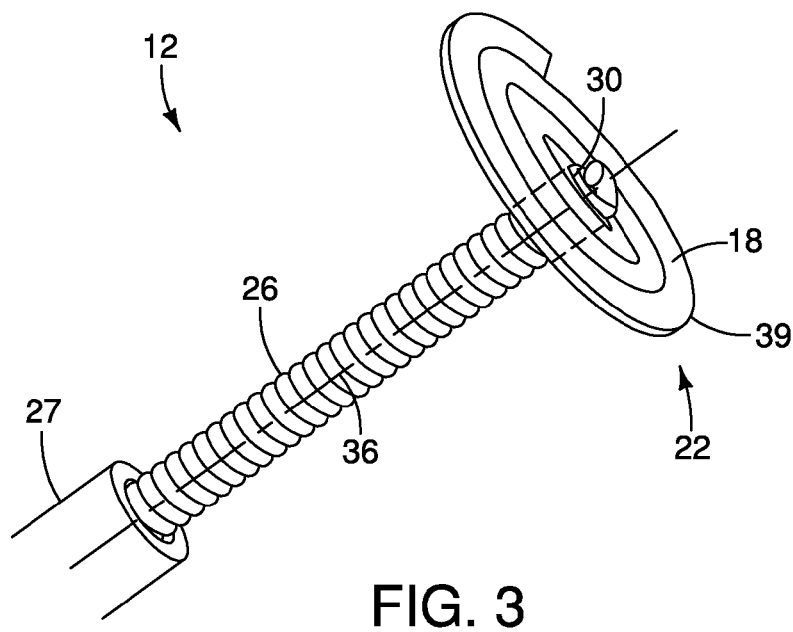
FIG. 3 is a partial perspective view of the expandable portion of the expandable biopsy device in a flattened configuration.
Figure 4:
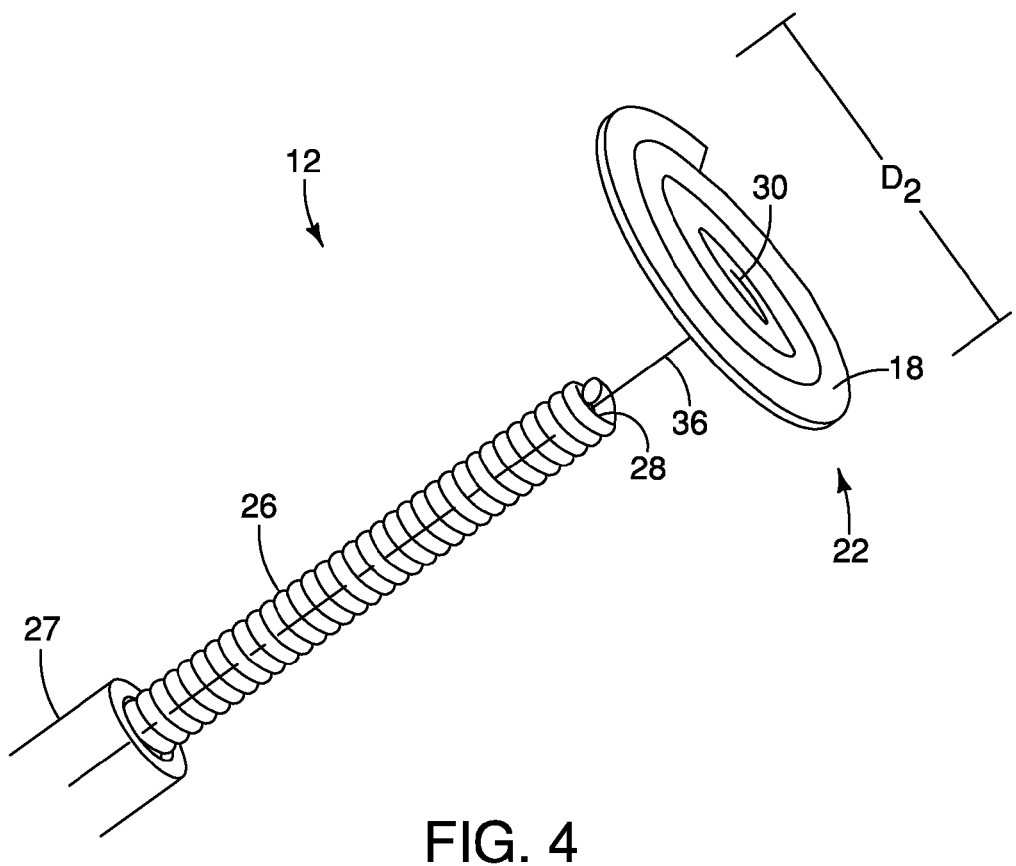
FIG. 4 is a partial perspective view of an embodiment of the expandable portion of the expandable biopsy device in a flattened configuration.

FIG. 1 illustrates an embodiment of an expandable biopsy device 10 in accordance with the present invention. The expandable biopsy device 10 includes an expandable portion 12 and a cutting portion 14. The expandable portion 12 is also shown in FIGS. 2-4. The expandable portion 12 includes an expandable plate member 18. The expandable plate member 18 has an expanded configuration 20 shown in FIGS. 1 and 2. In some embodiments the expanded configuration 20 may be spiral shaped and at least partially wound around a shaft 26. The expandable plate member 18 also has a flattened configuration 22 shown in FIGS. 3 and 4. The expanded configuration 20 of the expandable plate member 18 is longitudinally expanded relative to the flattened configuration 22 so that a length L1 in the expanded configuration is greater than a length L2 of the expandable plate member 18 in the flattened configuration 22. (Compare FIGS. 11 and 13.) In the flattened configuration, the expandable plate member 18 forms a substantially flat sheet of material that may be used supporting the tissue at the biopsy site. The expandable plate member 18 may be made from any material suitable for use in a patient and having sufficient strength to extend through a tissue. By way of non-limiting example, the expandable plate member may be made from nitinol or stainless steel. The expandable plate member 18 may formed in the expanded configuration 20 and delivered to a biopsy site in the expanded configuration 20 and then transitioned to the flattened configuration 22 once the expandable plate member 18 has been extended through the tissue to be biopsied as explained in more detail below. The expandable plate member 18 has a first diameter D1 measured at the widest part of the expandable plate member 18 in the expanded configuration 20. The expandable plate member 18 has a second diameter D2 in the flattened configuration 22. In some embodiments, D2 is greater than D1.

As shown in FIGS. 1-4, the expandable plate member 18 may be removably attached to the shaft 26. The shaft 26 may be a cable such as a torque cable suitable for rotatably inserting the expandable plate member 18 in the expanded configuration 20 through the tissue for obtaining a biopsy sample. As shown in FIG. 3, in some embodiments, a catheter 27 may also be provided to cover the shaft 26 so that the shaft 26 does not contact or injure the surrounding tissue as the shaft 26 is rotated to advance the expandable plate member 18 through the tissue. The catheter 27 may extend the full length of the shaft 26 or over a portion of the shaft 26. The shaft 26 may be removably attached to the expandable plate member 18 near or at a center portion 30 of the expandable plate member 18. The center portion 30 may include a tip 32 that may be pointed in some embodiments to facilitate insertion of the expandable plate member 18 into the tissue. The shaft 26 includes a lumen 28 extending at least partially through the shaft 26 as shown in FIG. 4. As shown in FIG. 3, the expandable plate member 18 may be collapsed to the flattened configuration 22 after the shaft 26 has been rotated to pass the expandable plate member 18 through the tissue. The shaft 26 may then be removed from the expandable plate member 18 as shown in FIG. 4.

In some embodiments, a cable 36 may be connected to the expandable plate member 18. The cable 36 may be any kind of cable including sutures and wires and the like. The cable 36 may be monofilament, braided, twisted or multifilament. The cable 36 may be attached to the expandable plate member 18 by any method known to one skilled in the art. By way of non-limiting example, the cable 36 may be welded, soldered, glued, taped and the like to the expandable plate member 18. The cable 36 is illustrated in FIG. 2 connected to the center portion 30 of the expandable plate member 18. In some embodiments, the cable 36 may be extended through the lumen 28 of the shaft 26 and connected to a handle (not shown) for controlling the movement of the cable 36. As shown in FIG. 4, the cable 36 may remain connected to the expandable plate member 18 when the shaft 26 is removed. The cable 36 may be used to facilitate flattening of the expandable plate member 18 to the flattened configuration 22 and for removal of the tissue sample as described in more detail below. A guide wire 40 may be used to the position the expandable portion 12 of the biopsy device 10 at the biopsy site.

The biopsy device 10 also includes the cutting portion 14 that is shown in FIGS. 1 and 5-7. The cutting portion 14 includes a blade 44 that may be movably positionable in a housing 46. The housing 46 includes an opening 51 and a cavity 47 formed in the housing 46 that is sized and shaped to hold the biopsy sample after the sample has been removed from the patient. The blade 44 may be moved to an exposed position 48 shown in FIGS. 6 and 7 where at least an edge 50 the blade 44 is extended distal to a distal end 52 of the housing 46 so that the blade 44 may contact the tissue. The edge 50 of the blade 44 is configured to cut the tissue to obtain a biopsy sample. The blade 44 may be releasably locked in position relative to the housing 46.

Figure 6:
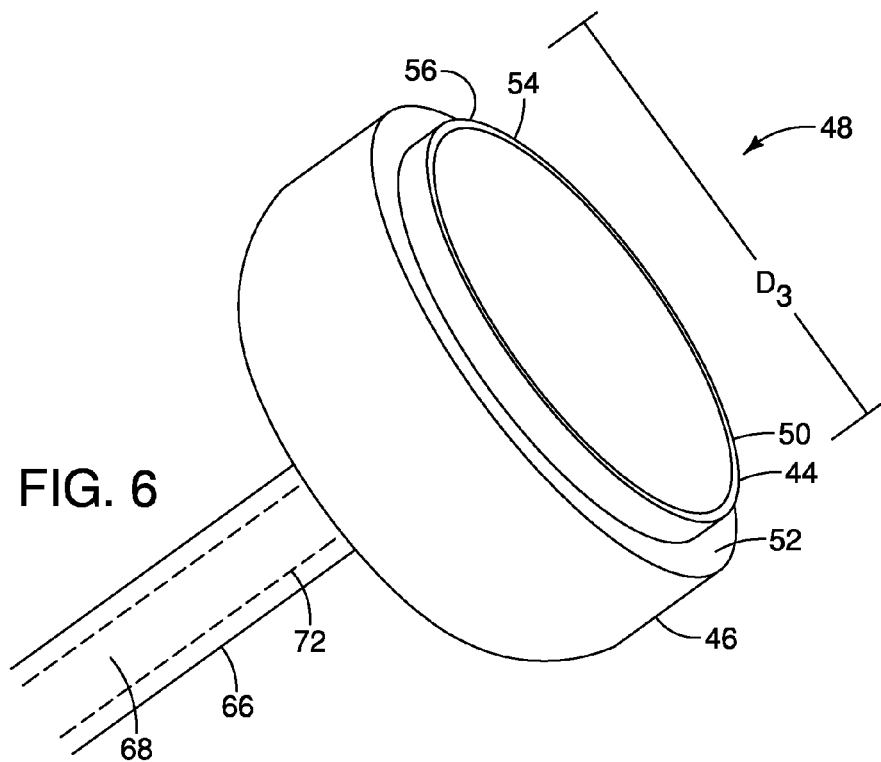
FIG. 6 is a perspective view of an embodiment of the cutting portion of the expandable biopsy device.
Figure 8:
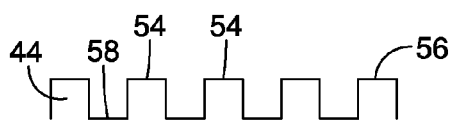
FIG. 8 is a partial side view of a blade of the cutting portion in accordance with an embodiment of the present invention.
Figure 7:
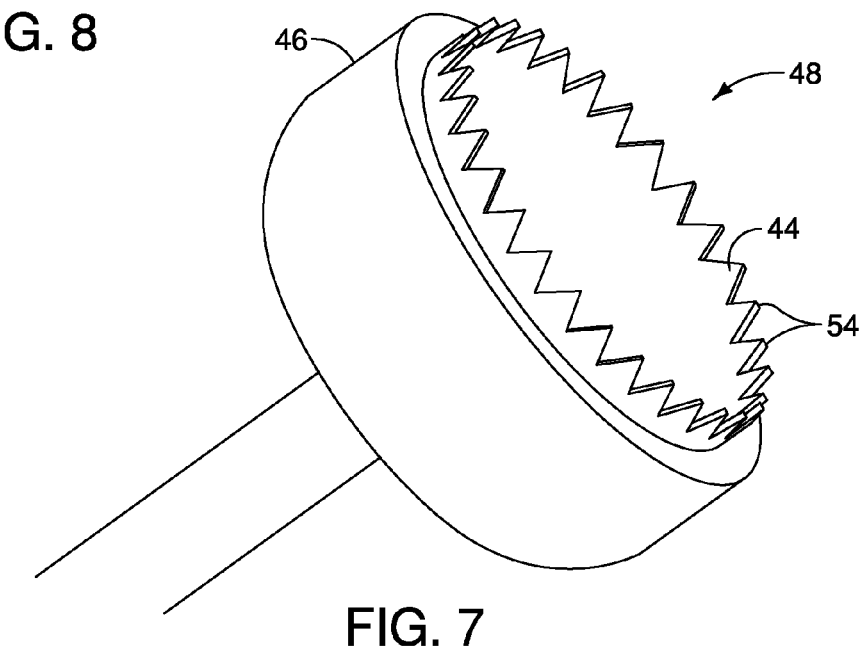
FIG. 7 is a perspective view of an embodiment of the cutting portion of the expandable biopsy device.

The blade 44 may be a single blade having a single cutting edge 54 as shown in FIG. 6 or the blade 44 may include a plurality of blade having a plurality of cutting edges 54 as shown in FIG. 7. Additional blade configurations may also be used including alternatively shaped cutting edges, straight edges, beveled edges and multiple blades, by way of non-limiting example. In some embodiments, the blade 44 may be include the cutting edge 54 around a perimeter 56 of the blade 44 or the blade 44 may include cutting edges 54 and non-cutting portions 58 where the housing 46 and the blade 44 or the blade 44 alone may be rotated to complete cutting a removable portion of tissue, see by way of non-limiting example, FIG. 8. The perimeter 56 of the blade 44 may be circular, oval, rectangular, square, or any other shape. The shape of the housing 46 may be the same as the shape of the perimeter 56 or different. As shown in FIG. 6, the blade 44 has a diameter D3 measured at the widest portion of the blade 44. The diameter D3 of the blade 44 is sized and shaped to be larger than the diameter D2 of the expandable plate member 18 in the flattened configuration 22 so that the blade 44 cuts around the tissue supported by the expandable plate member 18 as explained in more detail below. In some embodiments, the diameter D3 may be from about 0.5 mm to about 2 cm, although other diameters may also be used. The blade 44 may be made from any material suitable for use in a patient and having sufficient strength to extend through a tissue. By way of non-limiting example, the blade 44 may be made from nitinol or stainless steel.

Figure 5:
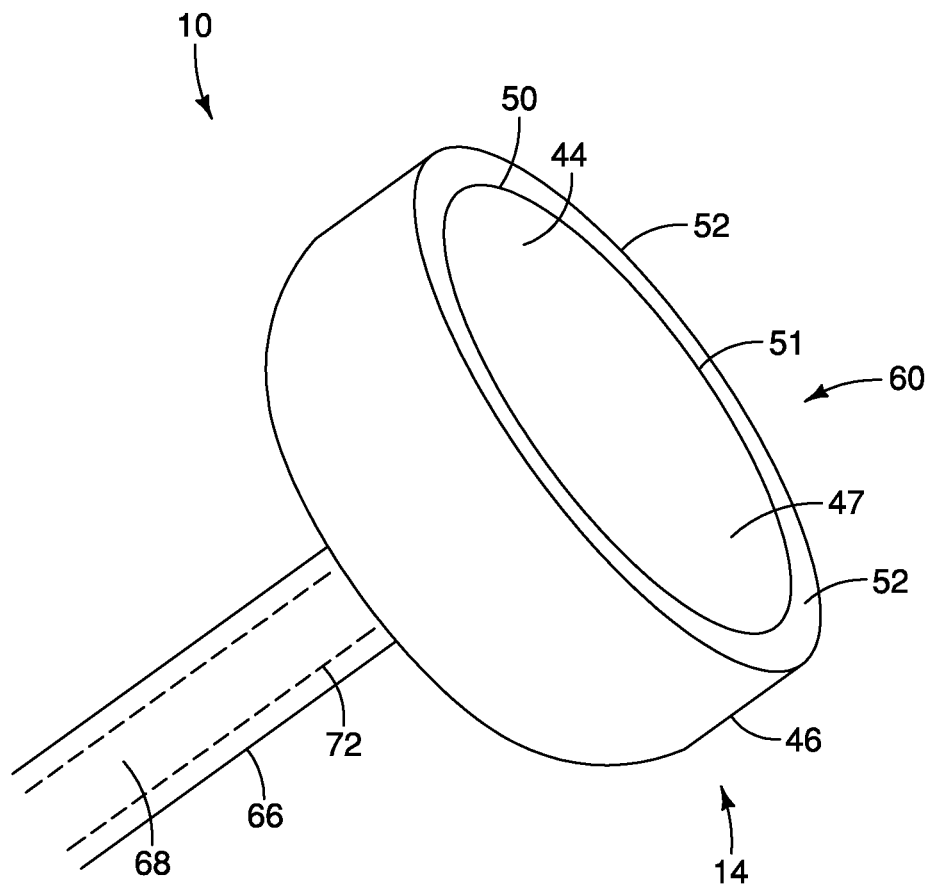
FIG. 5 is a perspective view of an embodiment of a cutting portion of the expandable biopsy device shown in FIG. 1.

The blade 44 may also be positioned in a protected position 60 as shown in FIG. 5 where the edge 50 of the blade 44 is positioned proximal to the distal edge 52 of the housing 46 so the blade 44 is not exposed to the tissue. The blade 44 may be positioned in the protected position 60 for delivery to the biopsy site and after the biopsy sample has been obtained for removal from the patient. In some embodiments, the blade 44 may be releasably locked in the protected position 60.

The cutting portion 14 may also include a shaft 66 configured to move the housing 46 within the patient. The shaft 66 includes a lumen 68 extending at least partially through the shaft 66. A drive cable 72 for movably positioning the blade 44 may extend through the lumen 68 of the shaft 66 as shown in FIGS. 5 and 6. In some embodiments, the drive cable 72 may be a torque cable suitable for rotating the blade 44 to cut into the tissue to obtain the biopsy sample. The drive cable 72 may also facilitate placement of the blade 44 against the tissue in the proper relationship to the expandable plate member 18 so that the blade 44 cuts around a perimeter 39 of the expandable plate member 18 that has been flattened against the tissue to be biopsied.

Figure 9:
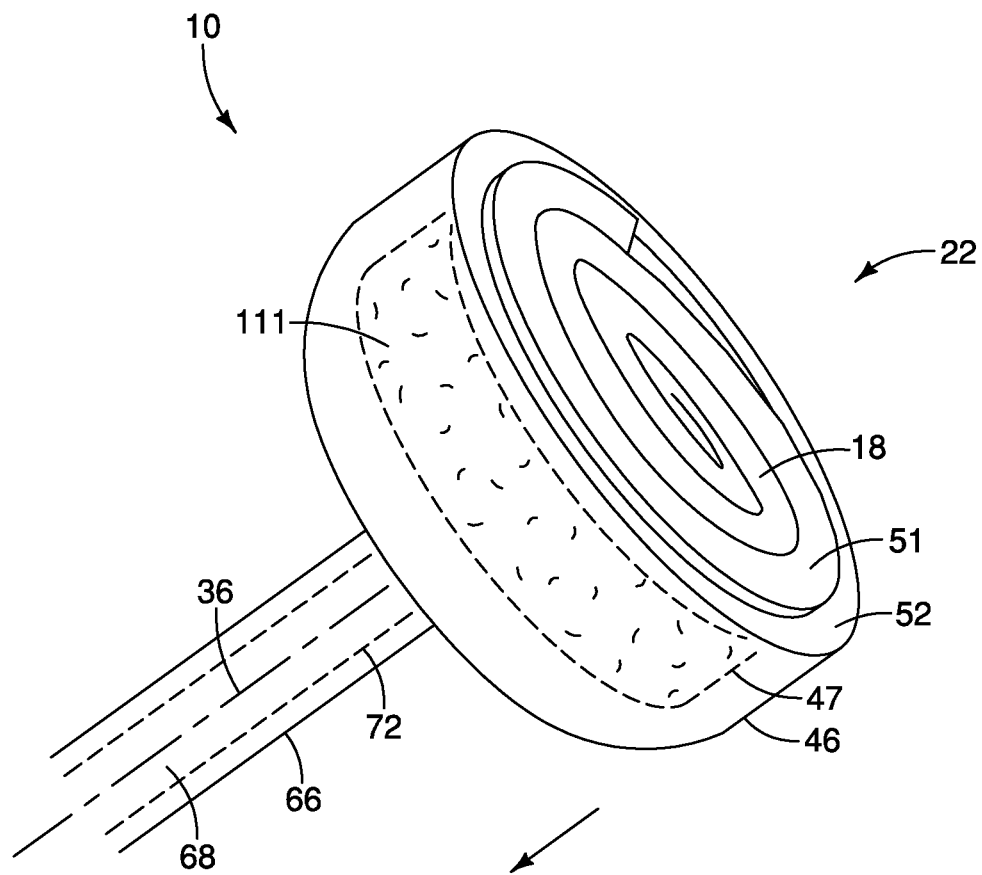
FIG. 9 is a perspective view of an embodiment of an expandable biopsy device in accordance with the present invention.

FIG. 9 illustrates the expandable plate member 18 in the flattened configuration 22 and positioned within the opening 51 of the housing 46 after a full thickness biopsy sample 111 has been removed from the patient and is contained within the cavity 47 of the housing 46. The blade 44 has been positioned proximal to the distal end 52 of the housing 46 and the expandable plate member 18 forms a cover over the cavity 47 to hold the sample in position as the biopsy device 10 is withdrawn from the patient. The cable 36 is connected to the expandable plate member 18 to place tension on the expandable plate member 18 to hold the expandable plate member 18 in the flattened configuration 22 while the biopsy device 10 is being withdrawn. In some embodiments, the cable 36 is extended through the lumen 68 of the shaft 66. In some embodiments, the cable 36 may be external to the lumen 68 or in a rapid exchange configuration.

Figure 10:
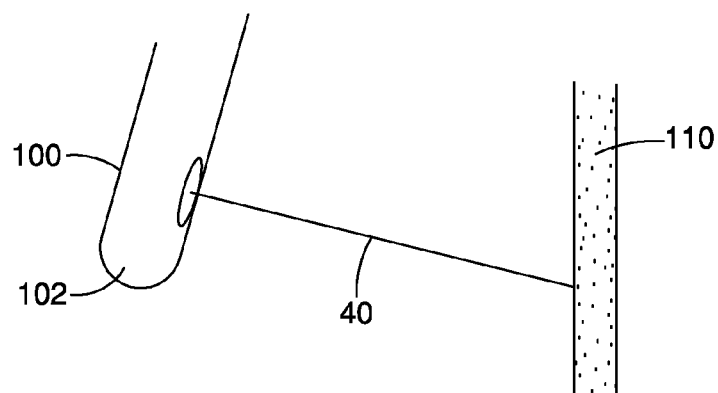
FIGS. 10-17 illustrate operation of an embodiment of the expandable biopsy device.
Figure 11:
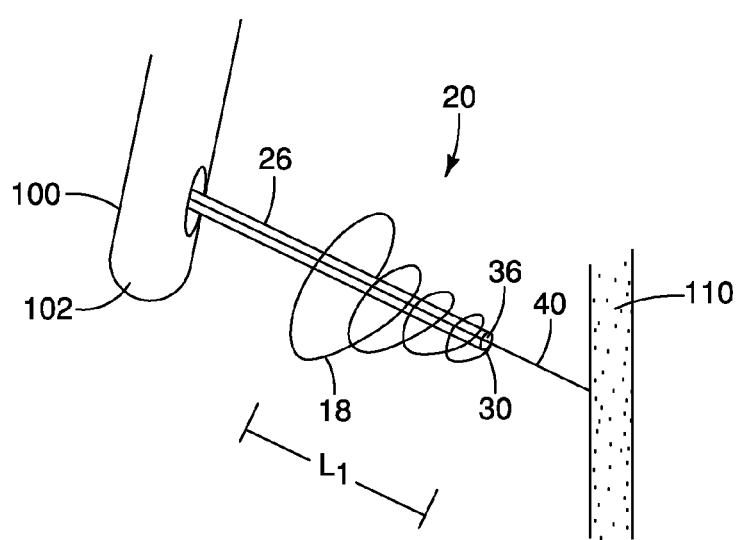
Figure 12:
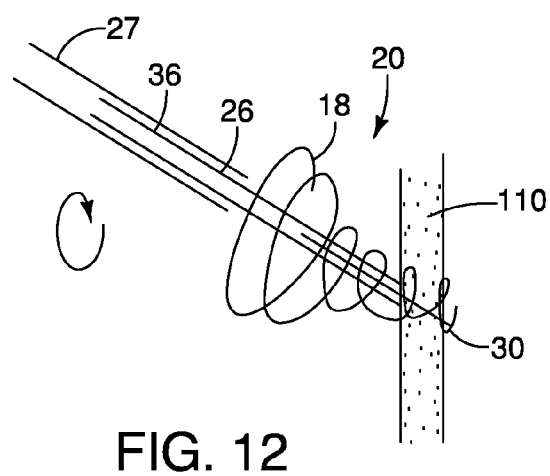

Operation of the expandable biopsy device will be explained with reference to the expandable biopsy device 10 as an example. Operation of the expandable biopsy device 10 is shown in FIGS. 10-17. FIG. 10 illustrates a tissue 110 of a patient where a full thickness biopsy through the tissue wall 110 is to be taken. A distal end 102 of an endoscope is shown with a wire guide 40 being directed to the tissue 110. FIG. 11 illustrates the expandable portion 12 of the biopsy device 10 that has been back loaded into the endoscope 100 and is being delivered to the tissue 110 over the guide wire 40. The expandable plate member 18 is in the expanded configuration 20 as the expandable portion 12 is being delivered to the tissue 110. In some embodiments, the expandable portion 12 may be delivered over the cable 36 to the biopsy site at the tissue 110. The cable 36 may have been previously secured to the tissue 110. FIG. 12 illustrates the expandable plate member 18 being rotatably positioned through the tissue wall 110 by rotation of the shaft 26. (Endoscope no longer shown.) A proximal portion of the shaft 26 may be connected to a rotatable handle (not shown) to drive the shaft 26 so that the tip 30 enters the tissue 110 and the remaining portion of the expandable plate member 18 enters and extends through the full thickness of the tissue 110. The catheter 27 is also shown positioned of the shaft 26 to protect the patient while the shaft 26 is rotatably advanced.

Figure 13:
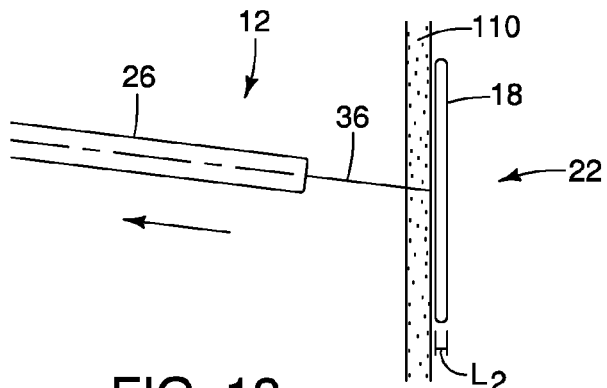
Figure 14:
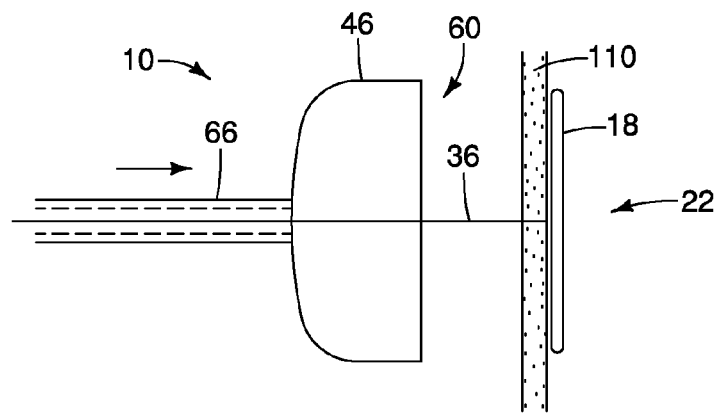
Figure 15:
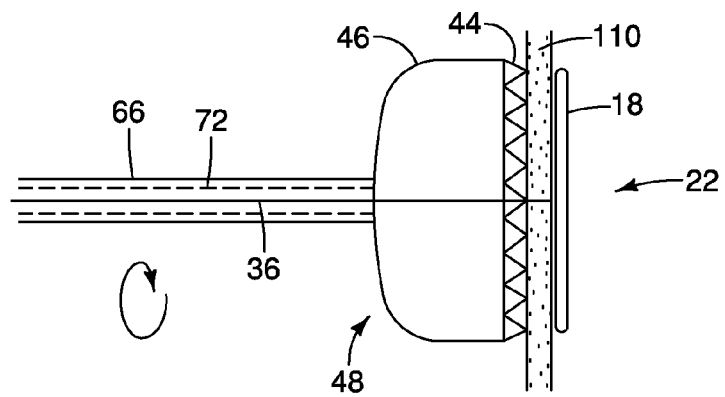

FIG. 13 illustrates the expandable plate member 18 fully advanced through the tissue 110 and positioned in the flattened configuration 22 against the tissue 110. The cable 36 may be tensioned to pull the expandable plate member 18 in the flattened configuration 22 and against the tissue 110. The shaft 26 is shown being proximally withdrawn from the expandable plate member 18. Once the shaft 26 is withdrawn, the cutting portion 14 of the biopsy device 10 may be back loaded into the endoscope for delivery to the biopsy site. FIG. 14 illustrates the cutting portion 14 being distally advanced to the tissue 110 over the cable 36. The blade 44 is in the protected position 60 within the housing 46. The shaft 66 may be used to advance the housing 46 and the blade 44 to the tissue 110. FIG. 15 illustrates the blade 44 in the exposed position 48 extended distal to the housing 46 and adjacent the tissue 110. The expandable plate member 18 is in the flattened configuration 22 and tension may be placed on the cable 36 to pull the expandable plate member 18 against the tissue 110 as the blade 44 is being advanced into the tissue 110 to cut a biopsy sample. In some embodiments, the blade 44 may be rotatably advanced through the tissue 110, for example by connecting the cable 72 to a drill or rotatable handle. The shaft 66 protects the surrounding tissue from the rotating cable 72.

Figure 16:
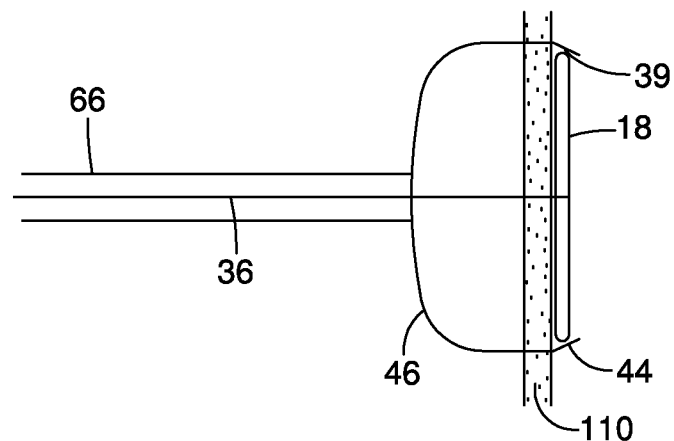
Figure 17:
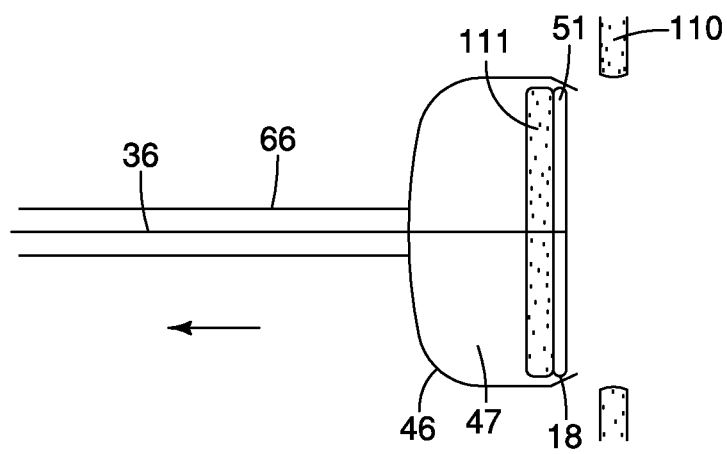

FIG. 16 illustrates the blade 44 that has cut through the tissue 110 and around the circumference 39 of the expandable plate member 18. The expandable plate member 18 is tensioned against the tissue 110 in the flattened configuration 22 to hold and support the tissue 110 as the blade 44 cuts through the full thickness of the tissue 110. FIG. 17 illustrates the removal of a full thickness biopsy sample 111 from the tissue 110. As shown, the expandable plate member 18 is in the flattened configuration 22 and is positioned within the opening 51 of the housing 46 to hold the sample 111 within the cavity 47 of the housing. The cable 36 and the shaft 66 are withdrawn proximally from the site of the tissue to remove the housing 46 and the expandable plate member 18. Since the blade 44 cuts around the perimeter 39 of the expandable plate member 18 that has a smaller diameter D2, the expandable plate member 18 can be withdrawn from the patient in the flattened configuration 22. The flattened configuration 22 allows the expandable plate member 18 to serve as a cover for the cavity 47 of the housing 46.

The above Figures and disclosure are intended to be illustrative and not exhaustive. This description will suggest many variations and alternatives to one of ordinary skill in the art. All such variations and alternatives are intended to be encompassed within the scope of the attached claims. Those familiar with the art may recognize other equivalents to the specific embodiments described herein which equivalents are also intended to be encompassed by the attached claims.

The invention claimed is:

1. An expandable biopsy device comprising:
   an expandable portion comprising an expandable plate member and a cable operably connected to the expandable plate member, the expandable plate member having a substantially flattened configuration and an expanded configuration, the expanded configuration being longitudinally elongated relative to the flattened configuration, the flattened configuration having a first diameter; and a cutting portion comprising a blade and a housing, the blade positionable at least partially within the housing, the blade having a second diameter, the housing comprising an opening and a cavity formed within housing; wherein the second diameter of the blade is greater than the first diameter of the expandable plate member in the substantially flattened configuration, and, wherein the expandable plate member in the expanded configuration is helically shaped.

2. The expandable biopsy device of claim 1, further comprising a shaft removably connected to the expandable plate member.

3. The expandable biopsy device of claim 2, wherein the shaft comprises a torque cable.

4. The expandable biopsy device of claim 1, wherein the expandable plate member comprises a central portion, the central portion forming a tip in the expanded configuration.

5. The expandable biopsy device of claim 1, wherein the expandable plate member is positionable in the opening of the housing in the flattened configuration.

6. The expandable biopsy device of claim 1, wherein the cable is connected to a central portion of the expandable plate member and the cable is configured to place tension on the expandable plate member in the flattened configuration.

7. The expandable biopsy device of claim 1, wherein a perimeter of the expandable plate member in the flattened configuration and the opening are substantially circular.

8. The expandable biopsy device of claim 1, wherein the blade is movably positionable relative to the housing from a protected position to an exposed position.

9. The expandable biopsy device of claim 1, wherein the blade comprises a plurality of teeth.

10. The expandable probe of claim 1, wherein the blade is connected to a cable and rotatable.

11. The expandable biopsy device of claim 1, wherein the cutting portion further comprises a cutting portion cable having a lumen extending at least partially therethrough, the cutting portion cable operably connected to the blade and the cable of the expandable portion extending through at least a portion of the lumen.

12. The expandable biopsy device of claim 1, wherein the expandable portion further comprises a catheter, the cable extending at least partially through a lumen of the catheter.

13. An expandable biopsy device comprising:
   an expandable portion comprising an expandable plate member, the expandable plate member having a substantially flattened configuration and an expanded configuration, the expanded configuration being longitudinally elongated relative to the flattened configuration, the flattened configuration having a first diameter; a housing comprising an opening at a distal portion of the housing, the expandable portion in the flattened configuration being sized and shaped to fit at least partially within the opening; and a cutting portion, the cutting portion positionable at least partially within the housing and having a blade distally extendable from the housing, the blade having a larger diameter than the first diameter; wherein the expandable portion is distally extendable relative to the housing in the expanded configuration and wherein the expandable plate member in the expanded configuration is helically shaped.

14. A method of biopsying a tissue sample, the method comprising:

positioning an expandable portion of a biopsy device at a tissue site; the expandable portion comprising an expandable plate member and a cable operably connected to the expandable plate member, the expandable plate member having a substantially flattened configuration and an expanded configuration wherein the expandable plate member in the expanded configuration is helically shaped; inserting the expandable plate member into the tissue site in the expanded configuration; proximally pulling on the cable and positioning the expandable plate member in the flattened configuration at the tissue site; advancing a cutting portion of the biopsy device toward the tissue site over the cable; advancing a blade of the cutting portion to the tissue site; and cutting the tissue sample while holding the expandable plate member against the tissue sample in the flattened configuration.

15. The method of claim 14, further comprising retaining the tissue sample within a cavity of a housing of the cutting portion with the expandable plate member at least partially covering an opening of the housing.

16. The method of claim 14, comprising rotatably extending the expandable plate member through a full thickness of the tissue at the tissue site.

17. The method of claim 14, comprising rotatably cutting the tissue sample with the blade at the tissue site.

18. The method of claim 14, rotatably positioning the expandable plate member in the expanded configuration through the tissue site with a cable removably connected to the expandable plate member.

19. The method of claim 18, further comprising removing the cable from the expandable plate member.

* * * * *